(12) United States Patent
Hsu et al.

(10) Patent No.: US 9,770,404 B2
(45) Date of Patent: Sep. 26, 2017

(54) COSMETIC COMPOSITION FOR WHITENING AND IMPROVING THE RESILIENCE OF SKIN

(75) Inventors: Kuan Chi Hsu, Yongin-si (KR); Hyeon Chung Kim, Seoul (KR); Sung II Park, Seoul (KR); Youn Joon Kim, Seoul (KR); Sang Hoon Han, Suwon-si (KR)

(73) Assignee: Amorepacific Corporation, Seoul (KR)

( * ) Notice: Subject to any disclaimer, the term of this patent is extended or adjusted under 35 U.S.C. 154(b) by 40 days.

(21) Appl. No.: 13/988,949

(22) PCT Filed: Nov. 21, 2011

(86) PCT No.: PCT/KR2011/008876
§ 371 (c)(1),
(2), (4) Date: May 22, 2013

(87) PCT Pub. No.: WO2012/074235
PCT Pub. Date: Jun. 7, 2012

(65) Prior Publication Data
US 2013/0243712 A1    Sep. 19, 2013

(30) Foreign Application Priority Data
Nov. 30, 2010   (KR) .................. 10-2010-0120263

(51) Int. Cl.
| A61K 8/97 | (2017.01) |
| A61K 8/65 | (2006.01) |
| A61Q 19/02 | (2006.01) |
| A61Q 19/08 | (2006.01) |
| A61K 8/73 | (2006.01) |

(52) U.S. Cl.
CPC .................. *A61K 8/97* (2013.01); *A61K 8/65* (2013.01); *A61K 8/73* (2013.01); *A61Q 19/02* (2013.01); *A61Q 19/08* (2013.01)

(58) Field of Classification Search
None
See application file for complete search history.

(56) References Cited

U.S. PATENT DOCUMENTS

| 5,663,160 A * | 9/1997 | Meybeck .................. A61K 8/49 514/182 |
| 2003/0103916 A1 * | 6/2003 | Imanaka et al. ................. 424/62 |
| 2003/0175315 A1 * | 9/2003 | Yoo .......................... A61K 8/06 424/400 |
| 2007/0065526 A1 * | 3/2007 | Gow et al. ..................... 424/728 |

FOREIGN PATENT DOCUMENTS

| CN | 101607982 A | * | 12/2009 | |
| JP | 2008086219 A | * | 4/2008 | |
| JP | 2010-150179 A | * | 7/2010 | |
| KR | 2004-0074154 | * | 8/2004 | |
| KR | 10-0466862 B1 | | 1/2005 | |
| KR | 10-0792629 B1 | | 1/2008 | |
| KR | 2006-0114416 | * | 1/2008 | |
| KR | 10-0825085 B1 | | 4/2008 | |
| KR | 20070032435 A | * | 4/2008 | |
| KR | 20080056554 A | * | 6/2008 | |
| KR | 10-0862979 B1 | | 10/2008 | |
| KR | 10-0965085 B1 | | 6/2010 | |
| WO | WO 2009057836 A1 | * | 5/2009 | ............... A61K 8/60 |
| WO | WO 2010/062087 | * | 6/2010 | |

OTHER PUBLICATIONS

English language machine translation of JP 2010-150179 A, 2013.*
English language machine translation of Park et al., KR 2009-017336 A, published Feb. 18, 2009, 2013.*
Korean Skin Care blog entry entitled "Sulwhasoo Snowise Whitening Line Review," Dec. 20, 2010; http://sulwhasoo-sulwhasoo.blogspot.com/2010/12/sulwhasoo-snowise-whitening-line-review.html.*
MSK online entry for "Oldenlandia diffusa," Jun. 28, 2013; http://www.mskcc.org/cancer-care/herb/oldenlandia-diffusa.*
Henderson Club advertisement "Snowise Whitening Serum," Jun. 2010; http://www.hldclub.com/en/pdf/enewsletter/24/018-019-life%20style-e.pdf.*
Lu (CN 1762324), SciFinder abstract accessed 2015.*
Lu (CN 1762324), Google Patents translation printed 2015.*
Kim "Effect of ginseng and ginsenosides on melanogensis and their mechanism of action," Journal of Ginseng Research 39:1-6, 2015.*
International Searching Authority International Search Report for PCT/KR2011/008876 dated May 22, 2012.

* cited by examiner

*Primary Examiner* — David J Blanchard
*Assistant Examiner* — Alissa Prosser
(74) *Attorney, Agent, or Firm* — Sughrue Mion, PLLC

(57) ABSTRACT

The present invention relates to a cosmetic composition for skin whitening and anti-aging, which contains 2 or more of collagen peptides, snake needle grass extract, and white ginseng saccharides as effective ingredients, improves skin resilience by increasing the content of collagen in the skin and suppresses the growth of melanin cells, improves skin brightness and uniformity, and alleviates skin yellowness and redness, so as to provide the effect of making the skin appear clearer and more radiant.

4 Claims, 1 Drawing Sheet

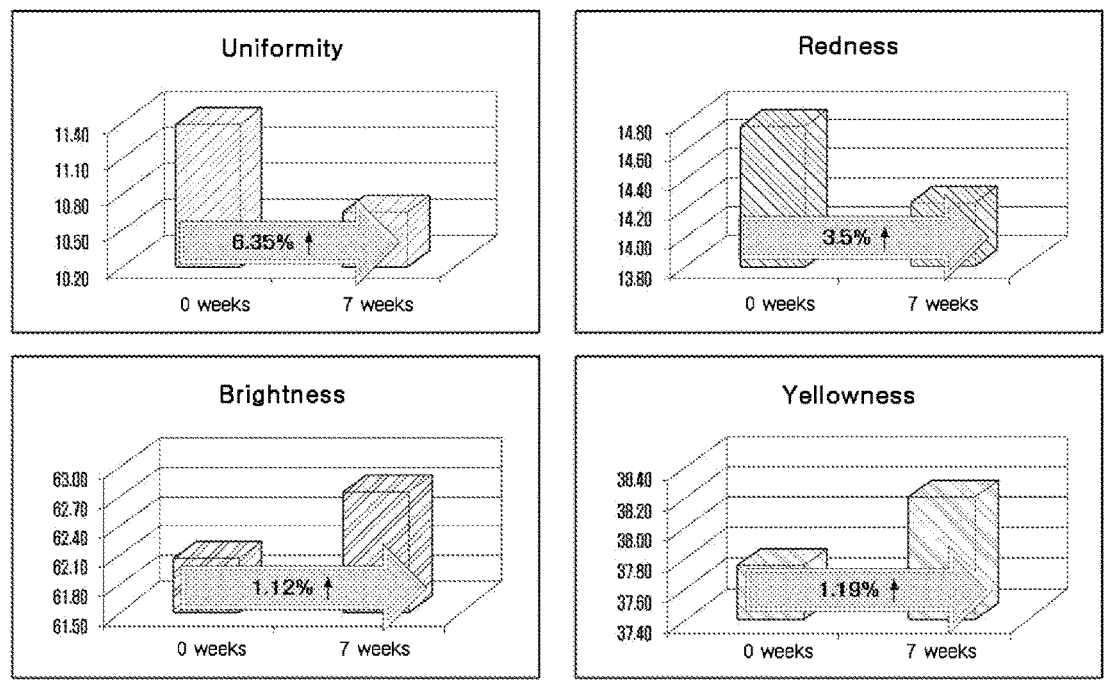

COSMETIC COMPOSITION FOR WHITENING AND IMPROVING THE RESILIENCE OF SKIN

TECHNICAL FIELD

The present invention relates to a cosmetic composition having the effects of whitening the skin and improving skin elasticity, and more particularly to a cosmetic composition for skin whitening and anti-aging, which contains two or more of a collagen peptide, an *Oldenlandia diffusa* extract and a white ginseng polysaccharide, which can improve skin elasticity by increasing the collagen content of the skin and inhibit the formation of melanocytes.

BACKGROUND ART

The human complexion is determined by melanin content (brightness and uniformity), yellowness and redness. Melanin that is present in the lowest portion of the skin's epidermal layer is produced in melanocytes. Melanin pigments are produced in melanocytes, have a dark brown color, and migrate the surface of the skin so as to be distributed in the horny layer. Thus, the melanin cells determine the skin color brightness and uniformity. Skin phenomena resulting from abnormal pigmentations caused by various factors such as UV rays and hormonal imbalance include darkness, discolorations, freckles, birthmarks, and dark spots.

Complexion can be greatly influenced not only by UV rays, but also by heat. When the skin is frequently exposed to heat, the activity of enzymes that remove reactive oxygen species (ROS) from the skin tissue is reduced so that toxic factors such as reactive oxygen species are not easily discharged and the skin looks yellowish. Also, when the skin is repeatedly exposed to heat for a long period of time, the elasticity of blood vessels decreases, and thus the redness of the skin can increase.

As age increases, the skin color brightness decreases, and the skin yellowness and redness increase. For this reason, when general complexions, including brightness, yellowness and redness, are improved, the effect of looking younger than actual age can be obtained.

A liquid crystal oil-in-water emulsion base containing a collagen peptide which is used in the present invention contains a stabilized collagen peptide in the base, and thus can increase skin elasticity to reduce light scattering into the skin to thereby reduce the shadowing phenomenon caused by the light scattering phenomenon, thereby providing a positive effect on skin brightness. However, with respect to this collagen peptide, only a cosmetic composition is known which reduces the stickiness of a solubilized formulation, reduces the absorption feeling and increases the long-term moisturizing ability, and there is no study or patent on the whitening effect of the collagen peptide.

In addition, an *Oldenlandia diffusa* extract is already known to have antioxidant, melanin inhibitory and collagen production-stimulating effects. When the collagen density of the dermal layer is increased, the density of the dermis is increased to reduce light scattering into the skin to thereby reduce the shadowing phenomenon caused by the light scattering phenomenon. Thus, in this case, the skin elasticity and brightness can be increased.

Meanwhile, it is known that the use of *Oldenlandia diffusa* extract in combination with beta-hydroxy acid (BHA) and an *Ophiopogon Japonicus* root extract inhibits the formation of skin melanocytes and prevents or alleviates skin pigmentations, including spots, freckles and discolorations, to provide skin whitening effects. However, it is not yet known that the *Oldenlandia diffusa* extract has the effect of improving complexion by reducing melanin and alleviating the skin yellowness and redness.

As used herein, the term "white ginseng polysaccharide" refers to a water-soluble polysaccharide extracted from dried fresh ginseng. Generally, about 7% white ginseng polysaccharide can be extracted from white ginseng, and the white ginseng polysaccharide has the effect of increasing the ATP energy of skin cells.

DISCLOSURE

Technical Problem

Accordingly, the present inventors have made efforts to find raw materials capable of effectively improving the skin elasticity, uniformity and brightness and alleviating the skin yellowness and redness, and as a result, have found that, when a liquid crystal oil-in-water emulsion base containing a collagen peptide is used in combination with an *Oldenlandia diffusa* extract or a white ginseng polysaccharide, it shows the effects of increasing the collagen density of the dermal layer, inhibiting melanin biosynthesis to improve the skin uniformity and brightness, and alleviating the skin yellowness and redness, thereby completing the present invention.

Therefore, it is an object of the present invention to provide a cosmetic composition for whitening the skin and improving skin elasticity, which effectively improves the skin uniformity, brightness, yellowness, redness and elasticity.

Technical Solution

In order to accomplish the above object, the present invention provides a cosmetic composition containing, as active ingredients, two or more of a collagen peptide, an *Oldenlandia diffusa* extract and a white ginseng polysaccharide.

Advantageous Effects

The cosmetic composition of the present invention improves the skin uniformity and brightness and the collagen density of the dermal layer and alleviates the skin yellowness and redness to improve complexion, thus making the skin looking more elastic, clearer and brighter.

DESCRIPTION OF DRAWINGS

FIG. 1 shows the results of evaluation (clinical test) of the skin brightness, uniformity, yellowness and redness on the human body using compositions of Example 3 and Comparative Example 1 for 7 weeks.

BEST MODE

The cosmetic composition of the present invention contains, as an active ingredients, two or more of a collagen peptide, an *Oldenlandia diffusa* extract and a white ginseng polysaccharide.

The collagen peptide that is used in the present invention may be contained in a liquid crystal oil-in-water emulsion base, and when the liquid crystal oil-in-water emulsion base containing the collagen peptide is used in combination with an *Oldenlandia diffusa* extract and a white ginseng polysaccharide, it can show synergistic effects on skin elasticity and whitening.

The liquid crystal oil-in-water emulsion base that is used in the present invention may contain two or more selected from the group consisting of sorbitan stearate, sorbitan laurate, behenyl alcohol, cetearyl alcohol, caprylic/capric triglyceride, cetearyl glucoside, polyglyceryl-10 pentastearate, and sodium stearoyl lactylate.

As used herein, the term "collagen" refers to a protein constituting connective tissue in the skin, tendons, bones and cartilages. It is a very important fibrous protein (albuminoid) placed between cells in the body of animals, including humans. Collagen is a polymer protein having a helix structure consisting of three polypeptide chains, each having a molecular weight of about 100,000. It improves the immune function of the human body, promotes the regeneration of cells to strengthen joints, and increases the metabolic activity and moisture-holding capacity of the skin to significantly improve skin beauty.

Collagen peptides that are generally used are difficult to absorb transdermally, because they have a molecular weight ranging from tens of thousands to hundreds of thousands. However, the collagen peptide that is used in the present invention is a component having a molecular weight of about 1,000, prepared by hydrolyzing collagen having a molecular weight of about 100,000. It is easily absorbed into the skin due to its low molecular weight to reduce wrinkles and promote cell regeneration, and has excellent skin affinity and moisturizing ability.

The collagen peptide that is used in the present invention can be prepared according to any conventional method known in the art, and the preparation method is not specifically limited. For example, the collagen peptide that is used in the present invention is prepared by a method comprising the steps of: (1) hydrolyzing collagen derived from the scales of marine fishes grown in a clean environment; (2) removing immunity-inducible components from the hydrolyzed collagen; and (3) reducing the molecular weight of the collagen of step (2).

The collagen peptide of the present invention is contained in an amount of 0.001-0.05 wt % based on the total weight of the composition. If the content of the collagen peptide is less than 0.001 wt %, the skin beauty effect thereof will be insignificant, and if the content of the collagen peptide is more than 0.05 wt %, the stability thereof in the liquid crystal base will be poor.

The *Oldenlandia diffusa* extract that is used in the present invention may be prepared by any method known in the art, and the preparation method is not specifically limited. For example, 1 kg of the dried whole plant of *Oldenlandia diffusa* is added to 10 liters of purified water, and then it is heated until boiling and is further heated for 10 minutes. After removing the water, the residue is washed, and then further washed by adding 10 liters of purified water thereto. Then, the residue is dried in air and added to 20 liters of 70% ethanol, after it is warmed and extracted under reflux in a reflux apparatus for 24 hours. After removing the solid using an 80-mesh sieve, the remaining filtrate is further filtered and concentrated, and the resulting solid is encapsulated in nanosomes. In this manner, the *Oldenlandia diffusa* extract can be obtained.

The *Oldenlandia diffusa* extract prepared as described above is contained in an amount of 0.001-10 wt %, and preferably 0.005-5.0 wt %, based on the total weight of the composition. If the content of the *Oldenlandia diffusa* extract is less than 0.001 wt %, it cannot show a distinct effect, and if the content of the *Oldenlandia diffusa* extract is more than 10.0 wt %, the increase in the content will not lead to a distinct increase in the effect.

The white ginseng polysaccharide that is used in the present invention may be prepared by any method known in the art, and the preparation method is not specifically limited. For example, dried white ginseng is added to purified water warmed to 60~80° C., and it is washed for 10-20 minutes while being stirred at intervals. The washed white ginseng is added to a 7:3 (w/w) mixed solvent of purified water warmed to 80~85° C.: 1,3-butylene glycol and is extracted for 6-8 hours while being stirred at intervals. The extract is cooled to 20~30° C. and filtered to remove the solid. In this manner, the white ginseng polysaccharide extract can be obtained.

The white ginseng polysaccharide prepared as described above is contained in an amount of 0.001-10 wt %, and preferably 0.005-5.0 wt %, based on the total weight of the composition. If the content of the white ginseng polysaccharide is less than 0.001 wt %, it cannot show a distinct effect, and if the content of the white ginseng polysaccharide is more than 10.0 wt %, the increase in the content will not lead to a distinct increase in the effect.

The cosmetic composition of the present invention may further contain an oil component. The oil component may be natural oil or synthetic oil. Specifically, the oil component may be a hydrocarbon, triglyceride, ester or silicone oil.

The oil component is contained in an amount of 1.0-40.0 wt %, and preferably 5.0-20.0 wt %, based on the total weight of the composition. If the content of the oil component is less than 1.0 wt %, it will be difficult to obtain a desired emulsion formulation, and if the content of the oil component is more than 40 wt %, the emulsion formulation will have poor stability.

The cosmetic composition of the present invention may be formulated as an oil-in-water (O/W) or water-in-oil (W/O) emulsion composition. In addition, it may be formulated in the form of lotion, cream, emulsion, patch, stick or spray.

The cosmetic composition of the present invention may further comprise, in addition to the above-described active ingredients, other components which are generally added to cosmetic compositions. Specific examples of these components include oils and fats, moisturizing agents, emollients, surfactants, organic and inorganic pigments, organic powder, UV absorbing agents, preservatives, disinfecting agents, antioxidants, plant extracts, pH adjusting agents, alcohols, dyes, fragrances, blood circulation stimulating agents, cooling agents, antiperspirants, purified water, and the like.

The composition of the present invention can increase the collagen content of the skin to increase skin elasticity to thereby inhibit skin aging. In addition, it can inhibit the formation of melanocytes to alleviate skin pigmentations, including spots, freckles and discolorations, and alleviate the skin yellowness and redness to improve the skin brightness and uniformity.

MODE FOR INVENTION

Hereinafter, the present invention will be described in further with reference to examples and test examples. It is to be understood, however, that these examples and test examples are for illustrative purposes only and are not intended to limit the scope of the present invention.

TEST EXAMPLE 1

Effect on Inhibition of Melanin Production

Human melanoma HM3KO cells (Y. Funasaka, Department of dermatology, Kobe university school of medicine, 5-1 Kusunoki-cho 7-chrome, Chuo-ku, Kobe 650, Japan) were added to 10% fetal bovine serum-containing minimum essential medium (MEM) and cultured under the conditions of 37° C. and 5% $CO_2$. The cultured cells were plated on T75 flasks at a density of $3 \times 10^5$ cells per flask and allowed to stand overnight until the cells adhered to the flask wall. After the cells have been confirmed to adhere to the flask wall, the medium was replaced with a fresh medium containing each of 10 ppm of an *Oldenlandia diffusa* extract, 10 ppm of a white ginseng polysaccharide and a mixture of 5 ppm of the *Oldenlandia diffusa* extract and 5 ppm of the white ginseng polysaccharide. In a control group, a DMSO-containing medium was used. While the medium was replaced with a fresh medium containing each test material at intervals of 2-3 days in this manner, the cells were cultured until the flask was filled with the cells. When the cells completely grew, the cells were collected, and the color thereof was compared between the control group and each of the groups treated with the test material. In addition, after the culture medium has been removed and the cells have been washed with PBS, the cells were dissolved in 1N sodium hydroxide, and the absorbance at 500 nm was measured. Based on the measurements, the percent inhibition of melanin production was calculated using the following equation 1, and the results of the calculation are shown in Table 1 below.

Percent inhibition of melanin production=100−(absorbance of each test material/absorbance of control×100)    Equation 1

TABLE 1

| Test material (each 0.1%) | Control | *Oldenlandia diffusa* extract | White ginseng extract | *Oldenlandia diffusa* extract + white ginseng extract |
|---|---|---|---|---|
| Inhibition % | 5 | 23 | 16 | 64 |

As can be seen in Table 1 above, when the *Oldenlandia diffusa* extract and the white ginseng extract were used alone, melanin production was inhibited. In addition, when the *Oldenlandia diffusa* extract and the white ginseng extract were used in combination, the effect on the inhibition of melanin production was higher than when the *Oldenlandia diffusa* extract and the white ginseng extract were used alone. This suggests that the *Oldenlandia diffusa* extract and the white ginseng extract, which are used in the present invention, have excellent effects on the inhibition of melanin production.

TEST EXAMPLE 2

Measurement of Effect on Collagen Biosynthesis

Human fibroblasts were cultured on a 24-well plate, and then the medium was replaced with a medium containing each test material at the concentration shown in Table 2 below, and the cells were cultured for 3 days. 0.5 ml of 10% fetal bovine serum-containing DMEM medium was added to each well, and then 10 µCi of L[2, 3, 4, 5-3H]-proline was added. After 24 hours, the medium and cells in each well were collected, washed with 5% TCA (trichloroacetic acid) solution, and dispensed into two test tubes. 1 Unit/µl of type I collagenase was added to one of the test tubes and incubated at 37° C. for 90 minutes, and the other test tube was stored at 4° C. Then, 0.05 ml of 50% trichloroacetic acid solution was added to each of the test tubes which were then allowed to stand at 4° C. for 20 minutes. Then, the content in each test tube was centrifuged at 12,000 rpm for 10 minutes, and the CPM (counts per minute) value of each supernatant and precipitate was measured using a liquid scintillation counter (LSC). Based on the measurements, the relative collagen biosynthesis value for each of the control group and the test groups was calculated using the following equation 2. In a control group, purified water was used in place of the test material. The results of the calculation were expressed relative to the control group (taken as 100) and are shown in Table 2 below.

$$RCB\ (\%) = \frac{\text{collagen}_{cpm}}{(\text{total collagen}_{cpm} - \text{collagen}_{cpm}) \times 5.4 + \text{collagen}_{cpm}} \times 100 \quad \text{Equation 2}$$

TABLE 2

Relative collagen biosynthesis (RCB) (%)

| Conc. (ppm) | Control | Collagen liquid crystal base | *Oldenlandia diffusa* | White ginseng polysaccharide | *Oldenlandia diffusa* + White ginseng polysaccharide | Collagen liquid crystal base + *Oldenlandia diffusa* | Collagen liquid crystal base + White ginseng polysaccharide | Collagen liquid crystal base + *Oldenlandia diffusa* + White ginseng polysaccharide |
|---|---|---|---|---|---|---|---|---|
| 10 | 100 | 128 | 115 | 105 | 140 | 158 | 142 | 167 |
| 1 | 100 | 105 | 103 | 101 | 106 | 107 | 106 | 110 |

As can be seen from the results in Table 2 above, the liquid crystal oil-in-water emulsion base containing the collagen peptide, the *Oldenlandia diffusa* extract and the white ginseng polysaccharide increased collagen biosynthesis in human skin cells in a concentration-dependent manner. The effect of promoting collagen biosynthesis was higher in the order of the liquid crystal oil-in-water emulsion base containing the collagen peptide >the *Oldenlandia diffusa* extract >the white ginseng polysaccharide. When two or more of these test materials were used in combination, a synergistic effect could be obtained, and when the liquid crystal oil-in-water emulsion base containing the collagen peptide, the *Oldenlandia diffusa* extract and the white ginseng polysaccharide were used in combination, the relative collagen biosynthesis (%) was the highest.

Because it can be seen that the density of skin tissue increases as the content of collagen increases, a test for the collagen density of the dermal layer in the human skin was performed in the following manner.

REFERENCE EXAMPLE 1

Preparation of Compositions of Examples 1 to 3 and Comparative Examples 1 to 4

Oil-in-water emulsion cosmetic compositions of Examples 1 to 3 and Comparative Examples 1 to 4, which have the compositions shown in Table 3 below, were prepared. The composition of Comparative Example 1 is a conventional oil-in-water emulsion cosmetic composition which does not contain the liquid crystal oil-in-water emulsion base containing the collagen peptide, the *Oldenlandia diffusa* extract and the white ginseng polysaccharide; the composition of Comparative Example 2 is a cosmetic composition which contains the liquid crystal oil-in-water emulsion base containing the collagen peptide, but does not contain the *Oldenlandia diffusa* extract and the white ginseng polysaccharide; and the cosmetic compositions of Comparative Examples 3 and 4 contain the *Oldenlandia diffusa* extract or the white ginseng polysaccharide. The cosmetic compositions of Examples 1 to 3 contain the liquid crystal oil-in-water emulsion base containing the collagen peptide, together with one or more of the *Oldenlandia diffusa* extract and the white ginseng polysaccharide. The liquid crystal oil-in-water emulsion base containing the collagen peptide was purchased from Chouette Co., Ltd. (Korea), and the *Oldenlandia diffusa* extract and the white ginseng polysaccharide were purchased from ACT Co., Ltd (Korea).

2) Components 3 to 9 in Table 3 above were mixed uniformly and dissolved by heating to 75° C.

3) The solution of step 2) was added slowly to the solution of step 1) with stirring (homomixing) at 70° C. to form an emulsion.

4) The emulsion of step 3) was cooled to 50° C. or below, and components 10 to 12 in Table 3 were added thereto and uniformly mixed, thereby preparing an oil-in-water emulsion cosmetic composition.

TEST EXAMPLE 3

Evaluation of Effect on Skin Elasticity

Thirty five Korean women in their 30s to 50s were divided into 7 groups, each consisting of 5 persons. Each of the cosmetic compositions of Examples 1 to 3 and Comparative Examples 1 to 4 was applied to each group twice a day everyday for 6 weeks, the skin conditions were comparatively analyzed by measuring the dermal compactness using Dermascan C. The results of the analysis are shown in Table 4 below.

TABLE 4

| Test material | Percent increase in dermal compactness | Percent increase in elastic feeling/ questionnaire |
|---|---|---|
| Example 1 | 30 | 49 |
| Example 2 | 39 | 55 |
| Example 3 | 46 | 59 |
| Example 4 | 35 | 50 |
| Comparative Example 1 | 6 | 3 |
| Comparative Example 2 | 23 | 30 |
| Comparative Example 3 | 19 | 23 |
| Comparative Example 4 | 20 | 21 |

As can be seen in Table 4, when the collagen peptide-containing liquid crystal oil-in-water emulsion base (Comparative Example 2), the *Oldenlandia diffusa* extract (Comparative Example 3) and the white ginseng polysaccharide (Comparative Example 4) were used alone, the collagen

TABLE 3

| No. | Raw material name | Example 1 | Example 2 | Example 3 | Example 4 | Comparative Example 1 | Comparative Example 2 | Comparative Example 3 | Comparative Example 4 |
|---|---|---|---|---|---|---|---|---|---|
| 1 | Purified water | To 100 | To 100 | To 100 | To 100 | To 100 | To 100 | To 100 | To 100 |
| 2 | Disodium EDTA | 0.05 | 0.05 | 0.05 | 0.05 | 0.05 | 0.05 | 0.05 | 0.05 |
| 3 | Cetearyl alcohol | 1 | 1 | 1 | 1 | 1 | 1 | 1 | 1 |
| 4 | Stearic acid | 0.5 | 0.5 | 0.5 | 0.5 | 0.5 | 0.5 | 0.5 | 0.5 |
| 5 | Glyceryl stearate/PEG-100 stearate | 1.5 | 1.5 | 1.5 | 1.5 | 1.5 | 1.5 | 1.5 | 1.5 |
| 6 | Polysorbate 60 | 1 | 1 | 1 | 1 | 1 | 1 | 1 | 1 |
| 7 | Squalane | 3.0 | 3.0 | 3.0 | 3.0 | 3.0 | 3.0 | 3.0 | 3.0 |
| 8 | Preservative | q.s. | q.s. | q.s. | q.s. | q.s. | q.s. | q.s. | q.s. |
| 9 | Fragrance | q.s. | q.s. | q.s. | q.s. | q.s. | q.s. | q.s. | q.s. |
| 10 | Collagen liquid crystal base | 1 | 1 | 1 | — | — | 1 | — | — |
| 11 | *Oldenlandia diffusa* extract | — | 3 | 3 | 3 | — | — | 3 | — |
| 12 | White ginseng polysaccharide | 3 | — | 3 | 3 | — | — | — | 3 |

Method for Preparation of Compositions of Examples 1 to 4 and Comparative Examples 1 to 4

1) Components 1 and 2 in Table 3 above were mixed uniformly and dissolved by heating to 70° C.

density of the dermis was increased. In addition, in the case of the composition of Example 3, which contains all the three test materials, the collagen density of the dermis significantly highly increased.

These results indicate that the inventive cosmetic composition containing a combination of the collagen peptide-containing liquid crystal oil-in-water emulsion base, the *Oldenlandia diffusa* extract and the white ginseng polysaccharide has the effect of increasing the collagen density of the dermal layer. In addition, the results of questionnaire (sensory evaluation) indicate that the inventive composition actually increased the elastic feeling.

TEST EXAMPLE 4

Effect on Whitening of Human Skin

In order to directly evaluate the skin whitening effects of the collagen peptide-containing liquid crystal oil-in-water emulsion base, the *Oldenlandia diffusa* extract and the white ginseng polysaccharide, thirty Korean women in their 30s to 50s (average age: 34.7) were divided into two groups, and each of the cosmetic compositions of Example 3 and Comparative Example 1 was applied to each group twice a day everyday for 7 weeks. The color of the skin was measured using a colorimeter (Minolta CR2002) in order to judge the effect of each composition on the skin conditions. Colors are indicated using the L*a*b* color system, in which the "L" value indicates brightness, the "b" value indicates yellowness, and the "a" value indicates redness. In addition, the uniformity of skin tone was measured using a spectrophotometer and comparatively analyzed. The results of the measurement are shown in FIG. 1.

As can be seen in FIG. 1, when the composition of Example 3 according to the present invention was used, skin brightness and uniformity were increased by 1.12% and 6.35%, respectively, compared to when the composition of Comparative Example 1 was used. In addition, yellowness and redness were improved by 1.19% and 3.5%, respectively.

The invention claimed is:

1. A method for whitening skin and increasing skin elasticity, comprising applying a cosmetic composition, which contains active ingredients consisting of an *Oldenlandia diffusa* extract, a collagen peptide, and a white ginseng polysaccharide, to the skin of a subject,
    wherein the collagen peptide is contained in a liquid crystal oil-in-water emulsion base,
    wherein the cosmetic composition is formulated into an oil-in-water emulsion,
    wherein each of the amounts of the *Oldenlandia diffusa* extract and the white ginseng polysaccharide is 0.001 to 10 wt %, respectively, based on the total weight of the composition,
    wherein the collagen peptide is contained in the amount of 0.001 to 0.05 wt % based on the total weight of the composition, and
    wherein the liquid crystal oil-in-water emulsion base is composed of two or more selected from the group consisting of sorbitan stearate, sorbitan laurate, behenyl alcohol, cetearyl alcohol, caprylic/capric triglyceride, cetearyl glucoside, polyglyceryl-10 pentastearate, and sodium stearoyl lactylate.

2. The method of claim 1, wherein the collagen peptide has a molecular weight of about 1,000 grams/mole.

3. The method of claim 1, wherein each of the amounts of the *Oldenlandia diffusa* extract and the white ginseng polysaccharide is 0.005-5 wt %, respectively, based on the total weight of the composition.

4. The method of claim 1, wherein the *Oldenlandia diffusa* extract is obtained by re-extracting with ethanol after extracting with boiling water, and the white ginseng polysaccharide extract is obtained by extracting with a mixed solvent of water and 1,3-butylene glycol.

* * * * *